Figure 1:
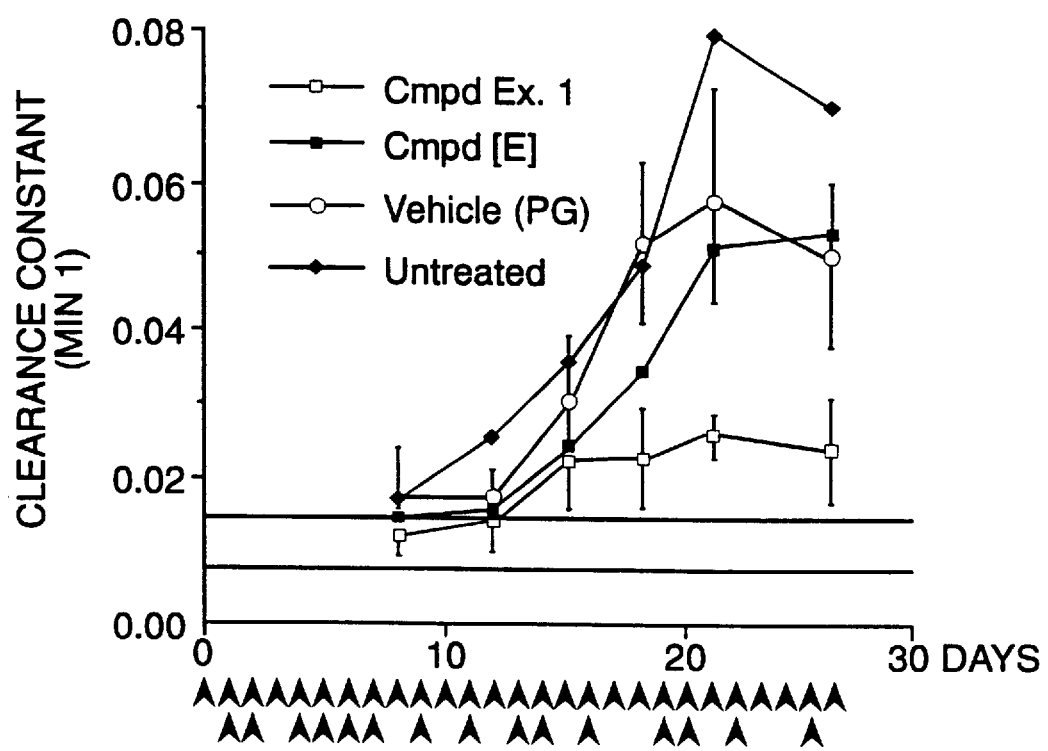

United States Patent [19]
Beeley et al.

[11] Patent Number: 5,827,890
[45] Date of Patent: Oct. 27, 1998

[54] SUCCINAMIDE DERIVATIVES, PROCESSES FOR THEIR PREPARATION AND THEIR USE AS GELATINASE AND COLLAGENASE INHIBITORS

[75] Inventors: Nigel Robert Arnold Beeley, Thame; Thomas Andrew Millican, Maidenhead, both of United Kingdom

[73] Assignee: Celltech Therapeutics Ltd., Slough, United Kingdom

[21] Appl. No.: 586,822

[22] PCT Filed: Aug. 2, 1994

[86] PCT No.: PCT/GB94/01697

§ 371 Date: Apr. 4, 1996

§ 102(e) Date: Apr. 4, 1996

[87] PCT Pub. No.: WO95/04033

PCT Pub. Date: Feb. 9, 1995

[30] Foreign Application Priority Data

Aug. 2, 1993 [GB] United Kingdom .................. 9315965
Jan. 11, 1994 [GB] United Kingdom .................. 9400377

[51] Int. Cl.$^6$ ......................... A61K 31/19; C07C 259/00
[52] U.S. Cl. ......................... 514/575; 514/616; 562/621; 564/139; 564/153
[58] Field of Search .................. 562/621; 564/153, 564/139; 514/575, 616

[56] References Cited

FOREIGN PATENT DOCUMENTS

| 0 497 192 | 8/1992 | European Pat. Off. . |
| 92 09 564 | 6/1992 | WIPO . |
| 92 09 565 | 6/1992 | WIPO . |

OTHER PUBLICATIONS

Stack et al., "Comparison of Vertebrate Collagenase and Gelatinase Using a New Flurogencic Substrate Peptide", Journal of Biological Chemistry, vol. 264, No. 8, (1989) pp. 4277–4281.

Moses et al., "Inhibitors of Angiogenesis", Bio/Technology, vol. 9 (1991) pp. 630–634.

Folkman et al., "Angiogenic Factors", Science, vol. 2, (1987) pp. 442–447.

Wahl et al., "Biocheistry and Inhibition of Collagenase and Stromelysin", Annual Reports in Medicinal Chemistry, No. 25, (1989) pp. 177–184.

*Primary Examiner*—Shailendra Kumar
*Attorney, Agent, or Firm*—Foley & Lardner

[57] ABSTRACT

Compounds of formula (1) are described, wherein $R^1$ represents (a), where $R^3$ is a hydrogen or halogen atom or a methyl, trifluoromethyl or methoxy group; $R^2$ represents a hydrogen atom or a methyl group; and the salts, solvates, hydrates and prodrugs thereof. The compounds are potent and selective orally active inhibitors of the metalloproteinase gelatinase with a long duration of action, and in particular inhibit angiogenesis in vivo. They can therefore be expected to be of use in the prophylaxis or treatment of angiogenesis dependent disorders such as solid tumours and arthritic diseases.

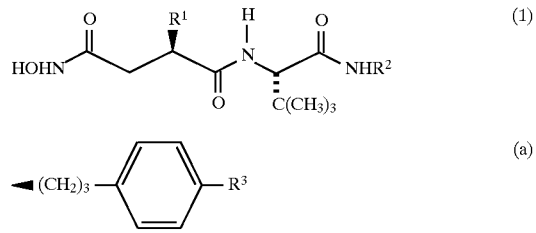

14 Claims, 1 Drawing Sheet

SUCCINAMIDE DERIVATIVES, PROCESSES FOR THEIR PREPARATION AND THEIR USE AS GELATINASE AND COLLAGENASE INHIBITORS

This application is a 371 of PCT/GB94/01697, filed Aug. 2, 1994.

This invention relates to $N^4$-hydroxy-$N^1$-(1-(S)-carbamoyl-2,2-dimethyl-propyl)-2-(R)-(4-chlorophenylpropyl)succinamide and analogues thereof, to processes for their preparation and to their use in medicine.

In normal tissues, cellular connective tissue synthesis is offset by extracellular matrix degradation, the two opposing effects existing in dynamic equilibrium. Degradation of the matrix is brought about by the action of proteinases released from resident connective tissue cells and invading inflammatory cells, and is due, in part, to the activity of at least three groups of metalloproteinases. These are the collagenases, the gelatinases (or type-IV collagenases) and the stromelysins. Normally these catabolic enzymes are tightly regulated at the level of their synthesis and secretion and also at the level of their extracellular activity, the latter through the action of specific inhibitors, such as $\alpha_2$-macroglobulins and TIMP (tissue inhibitor of metalloproteinase), which form inactive complexes with metalloproteinases.

The accelerated, uncontrolled breakdown of connective tissues by metalloproteinase catalysed resorption of the extracellular matrix is a feature of many pathological conditions, such as rheumatoid arthritis, corneal, epidermal or gastric ulceration; tumour metastasis or invasion; periodontal disease and bone disease. It can be expected that the pathogenesis of such diseases is likely to be modified in a beneficial manner by the administration of metalloproteinase inhibitors and numerous compounds have been suggested for this purpose [for a general review see Wahl, R. C. et al Ann. Rep. Med. Chem. 25, 175–184, Academic Press Inc., San Diego (1990)].

Although numerous metalloproteinase inhibitors have been described, many have not been suitable for further development as medicines since they have lacked any useful activity when administered orally at pharmaceutically acceptable doses. What is therefore needed is a potent and selective orally active compound. In our International Patent Specification WO 92/09564 we describe a class of peptidyl derivatives which are potent and selective inhibitors of gelatinase. We have now found that certain previously undisclosed members of this class of compounds have advantageously good oral bioavailability, and after oral administration have an advantageously longer duration of action than structurally closely related compounds.

Thus according to one aspect of the invention we provide a compound of formula (1)

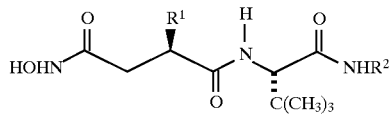

wherein $R^1$ represents

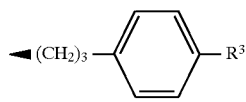

where $R^3$ is a hydrogen or halogen atom or a methyl, trifluoromethyl or methoxy group; $R^2$ represents a hydrogen atom or a methyl group; and the salts, solvates, hydrates and prodrugs thereof.

In the formulae herein, the ◄ line and the """" line are used to represent an unique configuration at an asymmetric centre When $R^3$ in the compounds of formula (1) is a halogen atom, it may be for example a fluorine, chlorine, bromine or iodine atom.

Salts of compounds of formula (1) include pharmaceutically acceptable salts, for example acid addition salts derived from inorganic or organic acids, such as hydrochlorides, hydrobromides, hydroiodides, p-toluene sulphonates, phosphates, sulphates, acetates, trifluoroacetates, propionates, citrates, maleates, fumarates, malonates, succinates, lactates, oxalates, tartarates and benzoates.

Salts may also be formed with bases. Such salts include salts derived from inorganic or organic bases, for example alkali metal salts such as sodium or potassium salts, alkaline earth metal salts such as magnesium or calcium salts, and organic amine salts such as morpholine, piperidine, dimethylamine or diethylamine salts.

Prodrugs of compounds of formula (1) include those compounds, for example esters, alcohols or amines, which are convertible, in vivo, by metabolic means, e.g. by hydrolysis, reduction, oxidation or transesterification, to compounds of formula (1).

In general in compounds of formula (1) $R^2$ is preferably a hydrogen atom.

Particularly useful compounds of formula (1) include those wherein $R^3$ represents a chlorine or fluorine atom or a methyl, trifluoromethyl or methoxy group. In general however compounds of formula (1) wherein $R^3$ represents a chlorine atom or a methyl or methoxy group are particularly preferred.

Important compounds according to the invention are:
  $N^4$-Hydroxy-$N^1$-(1-(S)-carbamoyl-2,2-dimethylpropyl)-2-(R)-4(chlorophenylpropyl)succinamide;
  $N^4$-Hydroxy-$N^1$-(1-(S)-carbamoyl-2,2-dimethylpropyl)-2-(R)-(4-methylphenylpropyl)succinamide;
  $N^4$-Hydroxy-$N^1$-(1-(S)-carbamoyl-2,2-dimethylpropyl)-2-(R)-(4-methoxyphenylpropyl)succinamide;
  $N^4$-Hydroxy-$N^1$-(1-(S)-carbamoyl-2,2-dimethylpropyl)-2-(R)-(4-trifluoromethylphenylpropyl)succinamide;
  and the salts, solvates, hydrates and prodrugs thereof.

A particularly important compound from among this group is:
  $N^4$-Hydroxy-$N^1$-(1-(S)-carbamoyl-2,2-dimethylpropyl)-2-(R)-(4-chlorophenylpropyl)succinamide and the salts, solvates and hydrates thereof.

The compounds according to the invention may be prepared by the following general processes, more specifically described in the Examples hereinafter. In the description and formulae below the groups $R^1$ and X are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable amino or hydroxyl protecting groups include benzyl, benzyloxycarbonyl or t-butoxycarbonyl groups. These may be removed from a protected derivative by catalytic hydrogenation using for example hydrogen in the presence of a metal catalyst, for example palladium on a support such as carbon in a solvent such as an alcohol e.g. methanol, or by treatment with trimethylsilyl iodide or trifluoroacetic acid in an aqueous solvent. Suitable carboxyl protecting groups include benzyl groups, which may be removed from a protected derivative by the methods just discussed, or alkyl groups, such as a t-butyl group which may be removed from a protected derivative by treatment with trifluoroacetic acid in an aqueous solvent. Other suitable protecting groups and methods for their use will be readily apparent. The formation of the protected amino, hydroxyl or carboxyl group may be achieved using standard alkylation or esterification procedures, for example as described below.

Thus according to a further aspect of the invention a compound of formula (1) may be prepared by reaction of an acid of formula (2)

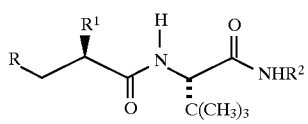

(2)

where R represents a —$CO_2H$ group or an active derivative thereof with hydroxylamine or an O-protected derivative or a salt thereof.

The reaction may be performed in an inert organic solvent such as an ether, e.g. a cyclic ether such as tetrahydrofuran, an amide e.g. a substituted amide such as dimethylformamide, or a halogenated hydrocarbon such as dichloromethane at a low temperature, e.g. −30° C. to ambient temperature, such as −20° C. to 0° C., optionally in the presence of a base, e.g. an organic base such as an amine, e.g. triethylamine or a cyclic amine such as N-methylmorpholine, followed where necessary by removal of any protecting group.

Active derivatives of acids of formula (2) include for example acid anhydrides, or acid halides, such as acid chlorides. Alternatively the acid may be reacted with a chloroformate for example ethylchloroformate, prior to reaction with the hydroxylamine. O-protected derivatives of hydroxylamine include for example O-silyl derivatives such as O-(alkyl)silyl derivatives e.g. O-(trimethylsilyl) hydroxylamine. Silyl protecting groups can be removed subsequent to the above reaction by treatment with an acid, e.g. a mineral acid such as hydrochloric acid.

Acids of formula (2) may be prepared by coupling an acid of formula (3)

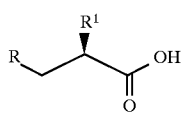

(3)

or an active derivative thereof, with an amine of formula (4)

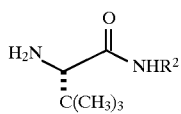

(4)

Active derivatives of acids of formula (3) include for example acid anhydrides, or acid halides, such as acid chlorides.

The coupling reaction may be performed using standard conditions for amination reactions of this type, for example those just described for the reaction of acids of formula (2) with hydroxylamine. Where an acid of formula (3) is used, the reaction may additionally be performed in the presence of a condensing agent, for example a diimide such as N,N'-dicyclohexylcarbodiimide, or 1-(3-dimethylaminopropyl)-3-ethylcarbodiimide, advantageously in the presence of a triazole such as 2-hydroxybenzotriazole. Alternatively, the acid may be reacted with a chloroformate for example ethylchloroformate, prior to reaction with the amine of formula (4).

Free carboxyl groups in the starting materials of formula (3) may need to be protected during the coupling reaction. Suitable protecting groups include t-butyl groups and those others mentioned above. Examples of the conditions necessary for the removal of such groups are also given above and in the Examples which follow.

The homochiral acids of formula (3) may be prepared in one process by oxidation of an oxazolidinone of formula (5)

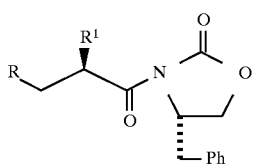

(5)

(where Ph is a phenyl group) using an oxidising agent such as a peroxide, e.g. hydrogen peroxide in a solvent such as an ether e.g. a cyclic ether such as tetrahydrofuran, at a low temperature, e.g. around 0° C. followed by treatment with a base, such as lithium hydroxide, at an elevated temperature.

In an alternative process, the acids of formula (3) may be prepared as described below for the preparation of a compound of formula (11).

The compounds of formula (5) may be prepared by reaction of an acyl halide $R^1CH_2COHal$ (where Hal is a halogen atom such as a chlorine, bromine or iodine atom) with a solution of (S)-4-(benzyl)-2-oxazolidinone in the presence of a base such as n-butyllithium in a solvent such as tetrahydrofuran at a low temperature, e.g. around −78° C., followed by treatment of the resulting oxazolidinone with a reagent $RCH_2Hal$ or a protected derivative thereof, in the presence of a base such as a silazide e.g. sodium hexamethyldisilazide or an amide, e.g. sodium bistrimethylsilylamide, at a low temperature.

Acyl halides $R^1CH_2COHal$ may be prepared by treatment of the corresponding acids $R^1CH_2CO_2H$ with conventional halogenating agents for example thionyl halides such as thionyl chloride under standard reaction conditions.

Intermediate acids of formula $R^1CH_2CO_2H$ are either known compounds or may be prepared by methods analogous to those used for the preparation of the known compounds. Thus for example acids of formula $R^1CH_2CO_2H$, wherein $R^1$ is a 4-substituted phenylpropyl group may be prepared by decarbonylation of a ketone of formula (6)

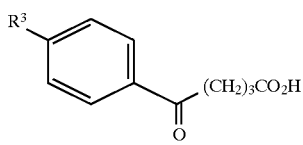

(6)

using hydrazine and potassium hydroxide in diethyleneglycol at elevated temperature, for example at around 220° C.

Ketones of formula (6) may be prepared by reaction of a mono substituted phenyl group with glutaric anhydride, using Friedel-Craft conditions, for example in the presence of aluminium bromide at room temperature.

Intermediate amines of formula (4) are either known compounds or may be made from known starting materials, using conventional manipulations. Thus in one example t-butylglycine azide may be treated, with ethylchloroformate and a base such as N-methylmorpholine, followed by reaction with aqueous ammonia and hydrogenation of the resulting azide in the presence of a catalyst, e.g. palladium on a support such as carbon, in a solvent such as ethanol, to yield an amine of formula (4) wherein $R^2$ is a hydrogen atom.

According to another aspect of the invention, a compound of formula (1) may be prepared by reaction of an acid of formula (7)

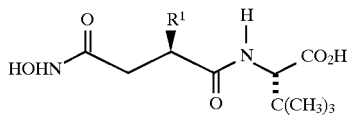

(7)

or an active derivative thereof with ammonia or methylamine.

Active derivatives of the acids of formula (7) include for example acid anhydrides, or acid halides, such as acid chlorides.

The coupling reaction may be performed using standard conditions for amination reactions of this type. Thus, for example the reaction may be carried out in a solvent, for example an inert organic solvent such as an ether, e.g. a cyclic ether such as tetrahydrofuran, an amide e.g. a substituted amide such as dimethylformamide, or a halogenated hydrocarbon such as dichloromethane at a low temperature, e.g. −30° C. to ambient temperature, such as −20° C. to 0° C., optionally in the presence of a base, e.g. an organic base such as an amine, e.g. triethylamine or a cyclic amine such as N-methylmorpholine. Where an acid of formula (7) is used, the reaction may additionally be performed in the presence of a condensing agent, for example a diimide such as N,N'-dicyclohexylcarbodiimide, advantageously in the presence of a triazole such as 1-hydroxybenzotriazole. Alternatively, the acid may be reacted with a chloroformate, for example ethyl chloroformate, prior to reaction with ammonia or methylamine.

Acids of formula (7) may be prepared by deprotecting a corresponding protected acid of formula (8)

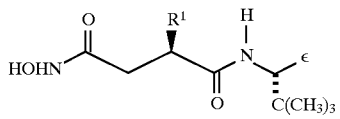

(8)

where ε is protected carboxylic acid, such as a carboxylic ester, for example a methyl ester —$CO_2CH_3$, using a base, e.g. lithium hydroxide, in an aqueous solvent, such as an alcohol, e.g. methanol, and water.

A compound of formula (8) may be prepared by reacting an acid of formula (9)

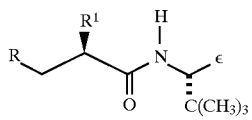

(9)

[where R is as previously defined] with hydroxylamine or an O-protected derivative or a salt thereof, using the reagents and conditions described above for the preparation of a compound of formula (1) from an acid of formula (2).

Acids of formula (9) may be obtained by mono-deprotection of a di-protected acid of formula (10)

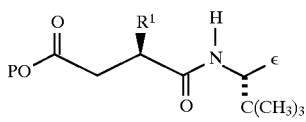

(10)

where P is a carboxylic acid protecting group, such as a t-butyl group, using for example an acid, such as trifluoroacetic acid.

Intermediates of formula (10) may be prepared by coupling an acid of formula (11)

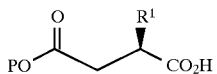

(11)

or an active derivative thereof, with an amine of formula (12)

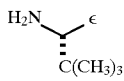

(12)

using similar conditions and reagents to those described above for the preparation of a compound of formula (2) from an acid of formula (3) and an amine of formula (4).

Amines of formula (12) may be prepared by protection of the free carboxyl group of a N-protected amino acid of formula (13)

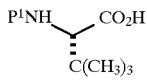

(13)

(where $P^1$ is an amine protecting group, such as a benzyloxycarbonyl group) followed by removal of the protecting group $P^1$, using for example a transfer hydrogenation, employing an organic hydrogen donor and a transfer agent.

Suitable hydrogen donors include for example acids, such as formic acid, formates, e.g. ammonium formate, alcohols, such as benzyl alcohol or ethylene glycol, hydrazine, and cycloalkenes such as cyclohexene or cyclohexadiene. The transfer agent may be for example a transition metal, for example palladium or platinum, optionally supported on an inert carrier such as carbon, nickel e.g. Raney nickel, ruthenium, e.g. tris(triphenylphosphine)ruthenium chloride or copper. The reaction may generally be performed at an ambient or elevated temperature, optionally in the presence of a solvent, for example an alcohol such as ethanol or an acid such as acetic acid.

The N-protected amino acids of formula (13) are either known compounds or may be made from known starting materials, using conventional manipulations.

Acids of formula (11) may be prepared by the reactions described above for the preparation of acids of formula (3) or by mono-deprotection of a di-protected di-acid of formula (14).

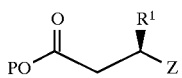

(14)

where Z is for example a benzyloxycarbonyl group, by hydrogenation, using for example hydrogen in the presence of a metal catalyst, such as palladium supported on carbon.

Intermediates of formula (14) may be prepared by coupling an intermediate of formula (15)

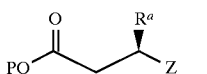

(15)

where $R^a$ is a 1-propenyl ($CH_2=CH-CH_2-$) group with a halobenzene derivative,

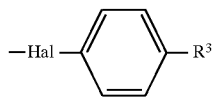

where Hal is a halogen atom such as a bromine atom.

The coupling reaction may be performed with a borane derivative, such as 9-borabicyclo[3.3.1]nonane (9BBN), in the presence of a palladium catalyst, such as tetrakistriphenylphosphine palladium or dichloro-[1,1'-bis(diphenylphosphino)ferrocene]palladium (II) and a base, e.g. sodium hydroxide, potassium carbonate or potassium phosphate, in a solvent such as tetrahydrofuran or dimethylformamide.

Intermediates of formula (15) may be prepared in a similar manner to the acids of formula (3) using an aryl halide $R^a CH_2 COHal$ with a solution of (S)-4-benzyl-2-oxazolidinone followed by treatment of the resulting oxazolidinone with a reagent $PO_2CH_2Hal$. The oxazolidinone is then cleaved with a base, such as n-butyllithium and the free acid group simultaneously protected as an ester Z by reaction with an alcohol, such as benzyl alcohol.

Salts of compounds of formula (1) may be prepared by reaction of a compound of formula (1) with an appropriate acid or base in a suitable solvent, e.g. an organic solvent such as an ether, using conventional procedures.

The compounds according to the invention are potent and selective orally active inhibitors of the metalloproteinase gelatinase and advantageously have a long duration of action when administered orally especially when compared to structurally closely related compounds such as those described in International Patent Specification No. WO 92/09564. The activity of the compounds may be determined by the use of appropriate enzyme inhibition tests, for example as described in Example A hereinafter or by oral administration to mice as described hereinafter in Example B. In our tests using this approach, compounds according to the invention have been shown to inhibit gelatinase with Ki values in the picomolar range.

The compounds according to the invention can be expected to be of use in the prophylaxis or treatment of diseases or disorders in which stromelysin, collagenase and, in particular, gelatinase have a role. Thus for example the compounds of formula (1) may be of use in the prophylaxis or treatment of musculo-skeletal disorders, for example arthritic diseases such as rheumatoid arthritis, osteoarthritis and septic arthritis, and to be of use to prevent tumour cell metastasis and invasion. The compounds may therefore be of use in the treatment of cancer, particularly in conjunction with radiotherapy, chemotherapy or surgery, or in patients presenting with primary tumours, to control the development of tumour metastasis. Particular cancers may include breast, melanoma, lung, head, neck or bladder cancers. Other uses to which the compounds of the invention may be put, include use for prevention of myelin degradation in the central and peripheral nervous system, for example in the treatment of multiple sclerosis, use for controlling peridontal diseases such as gingivitis, and use in tissue remodelling.

In one particular use, the compounds according to the invention advantageously inhibit angiogenesis in vivo, especially when administered orally. Thus, compounds according to the invention give substantial inhibition of angiogenesis when administered orally to mice, as described in Example C hereinafter. The degree of inhibition is much greater than that achieved with structurally related non-specific metalloproteinase inhibitors and represents a further unexpected advantage for compounds of the invention.

The compounds according to the invention can therefore be expected to be of use in the prophylaxis or treatment of angiogenic diseases. Such diseases may be characterised by the pathological growth of new capillaries [see, for example Folkman, J. and Klagsbrun, M. Science 235, 442–447 (1987) and Moses, M. A. and Langer, R. Bio/Technology 9, 630–634 (1991)]. Particular angiogenesis dependent diseases include solid tumours and arthritic diseases as described above, and, additionally, psoriasis, eye diseases such as the proliferative retinopathies, neovascular glaucoma and ocular tumours, angiofibromas, and hemangiomas.

For use in the above applications, the compounds of formula (1) may be formulated in a conventional manner, optionally with one or more physiologically acceptable carriers, diluents or excipients.

Thus according to a further aspect of the invention we provide a pharmaceutical composition comprising a compound of formula (1) and a pharmaceutically acceptable diluent, carrier or excipient.

Pharmaceutical compositions according to the invention include those for oral, buccal, parental or rectal administration or forms suitable for nasal administration or administration by inhalation or insufflation. Pharmaceutical compositions for oral use are particularly preferred.

In a still further aspect the invention provides a process for the production of a pharmaceutical composition according to the invention comprising bringing a compound of formula (1) into association with a pharmaceutically acceptable diluent, carrier or excipient.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles, and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (1) may be formulated for parental administration by injection e.g. by bolus injection or continuous infusion. Formulations for injection may be presented in unit dosage form. The compositions for injection may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of formula (1) may also be formulated in rectal compositions such as suppositories or retention enemas, e.g. containing conventional suppository bases such as cocoa butter or other glycerides.

In addition to the formulations described above the compounds of formula (1) may also be formulated as a depot preparation. Such long acting formulations may be administered by implantation or by intramuscular injection.

For nasal administration or administration by inhalation the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispenser device may be accompanied by instructions for administration.

The doses of compounds of formula (1) used in the above applications will vary depending on the disease or disorder and condition of the patient to be treated and the frequency of the dosing. In general however, oral and other doses may be in the range around 0.5 mg to 100 mg/kg body weight, particularly from about 1 mg to 50 mg/kg body weight. Dosage units may be varied according to the route of administration of the compound in accordance with conventional practice.

The compounds according to the invention are particularly useful for the prophylaxis or treatment of angiogenesis dependent diseases, for example those described above. Thus according to a further aspect of the invention we provide a method for the prophylaxis or treatment of an angiogenesis dependent disease in humans which comprises administering an effective dose of a compound of formula (1) to a subject with a disease associated with angiogenesis. Effective doses may be for example those just discussed above.

The invention is further illustrated in the following non-limiting Examples.

In the Examples, the following abbreviations are used:
RT—room temperature; DMF—dimethylformamide; THF—tetrahydrofuran; TFA—trifluoroacetic acid; EtOAc—ethyl acetate; MeOH—methanol.

INTERMEDIATE 1

4-t-Butyl Hydrogen 2-(4-Methylphenylpropyl) succinate (a) (S)-3-[1-Oxo-5-(4-methylphenyl)pentyl]-4-benzyl-2-oxazolidinone (1)

n-Butyllithium (1.6M solution in hexanes, 4.4 mmol, 2.75 ml 1.2 equiv.) was added dropwise to a solution of (S)-4-benzyl-2-oxazolidinone (3.64 mmol, 0.64 g) in THF (15 ml) at −78° C., under $N_2$ atmosphere. The orange solution was stirred for 30 min at −78° C. and then a solution of p-tolylvaleryl chloride (4.06 mmol, 0.86 g) in THF (5 ml) was added dropwise. The reaction mixture was stirred at −78° C. for 2 hr before quenching at −78° C. with a solution of brine—10% aqueous HCl (1:1, 10 ml). On warming to ambient temperature the reaction mixture was partitioned between EtOAc and water. The aqueous layer was separated and extracted twice with EtOAc. The combined organic layers were washed once with brine, once with sodium bicarbonate solution then dried ($MgSO_4$). The solvent was removed under vacuum to give a brown oil which was purified on silica gel (Merck 9385) eluting with 20% EtOAc/hexane to give the title compound (1) (0.65 g) as a slightly yellow oil. $\delta_H$ ($CDCl_3$) 1.63 (4H, m), 2.31 (3H, s), 2.62 (2H, m), 2.75 (1H, dd), 2.89–2.98 (2H, m), 3.26 (1H, dd), 4.12–4.18 (2H, m), 4.61–4.67 (1H, m), and 7.17–7.36 (9H, m).

(b) 3-[1-Oxo-2-(R)-(t-butylacetyl)-5-(4-methylphenyl)-pentyl]-4-(S)-benzyl-2-oxazolidinone (2)

A solution of the oxazolidinone (1) (0.65 g, 1.85 mmol) in THF (10 ml) was added to a solution of sodium bis (trimethylsilyl)azide (1M solution in THF, 2.6 mmol, 2.6 ml, 1.4 eq) in THF (10 ml) at −78° C. under nitrogen. The reaction mixture was stirred at this temperature for 1 hr and then t-butyl-bromoacetate (5.6 mmol, 1.08 g, 0.90 mg, 3 eq) was added dropwise. The reaction was allowed to warm to −20° C. and stirred at this temperature for 4 hr. The reaction was quenched at −78° C. with a solution of brine—10% HCl acid (1:1 ml, 10 ml). The mixture was partitioned between EtOAc and water. The aqueous layer was separated and extracted twice with EtOAc. The combined EtOAc layer was washed once with brine and once with $NaHCO_3$ solution, dried ($MgSO_4$) and the solvent removed to give a yellow oil, which was purified on Silica gel (Merck 9385) eluting with 20% EtOAc/hexane to give the title compound (2) (0.57 g). $\delta_H$ ($CDCl_3$) 1.42 (9H, s), 1.57–1.62 (2H, m), 2.30 (3H, s), 2.41–2.85 (5H, m), 3.33 (1H, dd), 4.10–4.25 (1H, m), 7.01–7.09 (4H, m), and 7.22–7.37 (5H, m).

(c) 4-t-Butyl Hydrogen 2-(4-Methylphenylpropyl) succinate (3)

A solution of the oxazolidinone (2) (0.57 g, 1.23 mmol) in THF/water (4:1, 25 ml) was cooled in an ice bath and treated with hydrogen peroxide solution (27.5 wt. %, 4.9 mmol, 0.56 ml, 4 eq). The mixture was stirred for a few min. then treated dropwise with a solution of lithium hydroxide monohydrate (1.23 mmol, 52 mg, 1.0 eq) in water (5 ml). The reaction was stirred for 1.5 hr then treated with a 10% aqueous solution of sodium sulphite (5 ml). The reaction mixture was adjusted to pH 12–13 with 1M NaOH and then partitioned between dichloromethane and water. The aqueous layer was separated and acidified with 10% HCl. The aqueous layer was extracted three times with EtOAc. The combined organic layer was washed once with brine, once with $NaHCO_3$ solution, dried ($MgSO_4$) and the solvent removed to give the title compound (3) (0.18 g) as a yellowish oil which was used without further purification. $\delta_H$ ($CDCl_3$) 1.43 (9H, s), 1.51–1.79 (4H, m), 2.32 (3H, s), 2.37 (1H, dd), 2.92 (1H, m), and 7.03–7.12 (4H, m).

INTERMEDIATE 2

4-t-Butyl Hydrogen 2-(4-Chlorophenylpropyl) succinate a) 5-(4-Chlorophenyl)-5-oxo-pentanoic acid To a stirred solution of aluminium bromide (300 g, 1.12 mol) in dry chlorobenzene (700 ml) at 4° C. was added a solution of glutaric anhydride (60 g, 0.526 mol) in chlorobenzene (300 ml). The resulting orange/yellow suspension was allowed to warm to RT, stirred overnight, then carefully poured into an ice cold stirred solution of 10% HCl (aqueous 1400 ml). The resulting white suspension was poured into EtOAc (900 ml) and the layers separated. The aqueous layer was washed with EtOAc (2×250 ml). The combined organic layer was washed with brine (1×400 ml), dried (MgSO$_4$) and the solvent removed in vacuo to give a yellow/white solid (115.74 g). Recrystallization from toluene/hexane (2:1, 750 ml) gave the title compound (95.14 g) as off white crystals.

b) 5-(4-Chlorophenyl)pentanoic acid

A mixture of the keto-acid (a) (94 g), potassium hydroxide and hydrazine monohydrate in diethylene glycol (550 ml) was heated to 150° C. The solution was refluxed at 150° C. for 4 hr and excess hydrazine removed by distillation at atmospheric pressure (internal temperature 165°–185° C.) before raising the temperature to 200° C. and heating for a further 3 hr. The reaction mixture was cooled and water (500 ml) added. A solution of 6M HCl (200 ml) was added dropwise to pH=1. The precipitate was extracted into EtOAc (500 ml) and the layers separated. The aqueous layer was washed with EtOAc (2×150 ml). The combined organic layer was washed with water (250 ml), brine (250 ml), dried (MgSO$_4$) and the solvent removed in vacuo to give the title compound (86.4 g).

c) 5-(4-Chlorophenyl)pentanoyl chloride

To a stirred solution of the acid (b) (86 g) in dry toluene (400 ml) was added dropwise, over 10 min, thionyl chloride (88 ml, 3 eq). The reaction mixture was stirred at RT for 2 hr, the solvent removed in vacuo and the remaining golden coloured oil azeotroped with dry toluene (2×50 ml), dry dichloromethane (2×50 ml) and the product left overnight on a freeze drier to give the title compound (93.5 g) as a light brown oil which was used in the next step without further purification.

d) (S)-3-[1-Oxo-5-(4-chlorophenyl)pentyl]-4-(S)-benzyl-2-oxazolidinone

Sodium hydride was washed, under N$_2$, with anhydrous toluene (2×125 ml) and suspended in anhydrous toluene (300 ml). (S)-(-)-4-Benzyl-2-oxazolidinone was dissolved in anhydrous THF (200 ml) and added to the sodium hydride suspension via cannula over 15 min. After a further 1 hr a solution of the chloride (c) (67.05 g) in anhydrous THF (300 ml) was added via cannula over 15 min and the mixture stirred for 4.5 hr at RT. A solution of saturated NaCl/1.0M HCl (1:1, 600 ml) was added carefully, the layers separated and the aqueous layer washed with EtOAc (2×100 ml). The combined organic layers were dried (MgSO$_4$) and the solvent removed in vacuo to give a creamy solid (99.1 g). Recrystallisation from EtOAc/hexane (2:8) gave the title compound (80.0 g) as a white solid.

e) 3-[1-Oxo-2-(R)-(t-butylacetyl)-5-(4-chlorophenyl)pentyl]-4-(S)-benzyl-2-oxazolidinone Prepared in a manner similar to Intermediate 1 b) from the above oxazolidinone 2d) (102 g), sodium bistrimethylsilylamide (300 ml, 0.33 mol) and t-butyl bromoacetate (98 ml, 0.605 mol). Recrystallisation from propan-2-ol gave the title compound (81 g) as a white crystalline solid.

f) 4-t-Butyl Hydrogen 2-(4-Chlorophenylpropyl) succinate

Prepared in a manner similar to Intermediate 1c) from the above oxazolidinone 2e), hydrogen peroxide (27.5% wt./vol, 0.199 mol, 24.6 ml, 2.75 eq.), lithium hydroxide monohydrate (0.079 mol, 79.42 ml, 1.1 eq) and sodium sulphite (100 ml). The title compound (24.78 g) was obtained as a white solid.

The following Intermediates 3 to 5 were prepared following the procedures described for the preparation of Intermediate 2 using (S)-4-(benzyl)-2-oxazolidinone and the appropriate acid chloride.

Intermediate 3=4-t-Butyl Hydrogen 2-(Phenylpropyl) succinate

Intermediate 4=4-t-Butyl Hydrogen 2-(4-Methoxyphenylpropyl) succinate

Intermediate 5=4-t-Butyl Hydrogen 2-(4-Fluorophenylpropyl) succinate

INTERMEDIATE 6 a) t-Butyl N-(1-(S)-Carbamoyl-2,2-dimethylpropyl)-3-(R)-4-chlorophenylpropyl)succinamoate To Intermediate 2 (2.05 g, 6.3 mmol) in dry DMF (30 ml) was added N-hydroxybenzotriazole hydrate (85 mg, 6.3 mmol), N-methylmorpholine (636 mg, 684 μl, 6.3 mmol), L-tert-leucinamide (1.22 g, 9.45 mmol) and 1-(3-dimethylaminopropyl)-3-ethyl carbodiimide hydrochloride (1.21 g, 6.3 mmol). The solution was stirred for 2 hr at RT, poured into 1.0M hydrochloric acid and EtOAc was added. The layers were separated and the acid layer extracted with EtOAc (3×50 ml). The combined organic layers were washed with NaHCO$_3$ (3×50 ml), brine (1×50 ml), dried (MgSO$_4$) and concentrated to give a yellowish oil. This was precipitated from ether/hexane to give the title compound (1.6 g) as a white solid. $\delta_H$ (CD$_3$OD) 1.01 (9H, s), 1.40 (9H, s), 1.50–1.62 (4H, m), 2.30 (1H, dd), 2.50–2.63 (3H, m), 2.75–2.85 (1H, m), 4.29 (1H, s), 7.12 (2H, d) and 7.22 (2H, d).

The following Intermediates were prepared in a similar manner to Intermediate 6a).

b) t-Butyl N-[1-(S)-methoxycarbonyl-2.2-dimethylpropyl]-3-(R)-(4-chlorophenylpropyl) succinamoate From Intermediate 2 and Intermediate 11. $\delta_H$ (CDCl$_3$) 0.95 (9H, s), 1.4 (9H, s), 1.5–1.7 (4H, m), 2.25–2.35 (1H, m), 2.5–2.7 (4H, m), 3.65 (3H, s), 4.45 (1H, d), 6.3 (1H, d), 7.05 (2H, d), and 7.2 (2H, d).

c) t-Butyl N-(1-(S)-methylaminocarbonyl-2.2-dimethylpropyl)-3-(R)-(4-methylphenylpropyl)succinamoate From Intermediate 1 (0.59 g) and Intermediate 9. $\delta_H$ (CDCl$_3$) 1.0 (9H, s), 1.4 (9H, s), 1.5–1.65 (5H, m), 2.4 (3H, s), 2.4 (3H, s), 2.5–2.65 (4H, m), 2.75 (3H, d), 4.15 (1H, d) and 7.05 (4H, m).

INTERMEDIATE 7 a) N-(1-(S)-Aminocarbonyl-2.2-dimethylpropyl)-3-(R)-(4-chlorophenylpropyl)succinamic acid To Intermediate 6 a) (1.9 g, 4.3 mmol) in TFA (18 ml) was added H$_2$O (2 ml). The solution was stirred at RT for 2 hr and the solvent removed under vacuum. The residue was precipitated from ether/hexane, filtered and dried (MgSO$_4$) to give the title compound (1.5 g). $\delta_H$ (CD$_3$OD) 1.01 (9H, m), 1.45–1.65 (4H, m), 2.47 (1H, dd), 2.55–2.70 (3H, m), 2.84–2.88 (1H, m), 4.30 (1H, d), 7.15 (2H, d), 7.22 (2H, d) and 7.74 (1H, d).

The following Intermediates were prepared in a similar manner to Intermediate 7a).

b) N-(1-(S)-Methoxycarbonyl-2.2-dimethylpropyl)-3-(4-chlorophenylpropyl)succinamic acid From Intermediate 6b) (1.3 g) in TFA (5 ml) and H$_2$O (1 ml). $\delta^H$ (CDCl$_3$) 0.95 (9H, s), 1.5–1.75 (4H, m), 2.45–2.7 (4H, m), 3.7 (3H, s), 4.45 (1H, d), 6.3 (1H, d), 7.05 (2H, d) and 7.25 (2H, d).

c) N-(1-(S)-Methylaminocarbonyl-2.2-dimethylpropyl)-3-(4-methylphenylpropyl)succinamic acid From Intermediate 6c) (0.57 g) $\delta_H$ (CDCl$_3$) 0.95 (9H, s), 1.4–1.55 (4H, m), 2.3 (3H, s), 2.5 (3H, m), 2.7 (5H, d), 4.4 (1H, d), 6.5 (NH, 1H, d), 7.0 (4H, m) and 7.6 (NH, 1H, d).

INTERMEDIATE 8

N-Methyl-2-(S)-benzyloxycarbonylamino-3.3-dimethyl-butanamide

N-Benzyloxycarbonyl tert-leucine (24.7 mmol, 6.56 g) was taken up in dry THF (50 ml) and the solution cooled to −40° C. under a nitrogen atmosphere. Ethyl chloroformate (26 mmol, 2.84 g) was added and the solution left to stir for 10 min. N-methylmorpholine (52 mmol, 5.24 g) was added and the solution stirred for 50 min between −20° C. and −40° C. before adding neat methylamine hydrochloride (24.7 mmol, 1.67 g). The solution was allowed to warm to RT and stirred at this temperature for 18 hr. The solution was poured into 10% HCl (50 ml), extracted with EtOAc (50 ml×3), the combined organic layer washed with saturated sodium bicarbonate solution (1×55 ml), then brine (1×50 ml), dried (MgSO$_4$) and the solvent removed in vacuo to give the title compound (5.72 g) as an off-white solid. $\delta_H$ (CDCl$_3$) 1.0 (9H, s), 2.75 (3H, d), 3.6 (1H, d), 5.0–5.1 (2H, m), 5.65 (1H, d), 6.25 (1H, s), 7.25–7.4 (5H, m) and 8.0 (1H, s).

INTERMEDIATE 9

N-Methyl-2-(S)-amino-3.3-dimethylbutanamide

Intermediate 8 (5.72 g) was taken up in MeOH (50 ml) and the solution degassed before adding Pd/C 10% (200 mg). The solution was left to stir under a hydrogen atmosphere for 2.5 hr, the catalyst filtered off through a silica plug and the solvent removed in vacuo to give the title compound (2.87 g) as a clear oil that went to a white solid once exposed to the air. $\delta_H$ (CDCl$_3$) 1.0 (9H, s), 2.80 (3H, d) and 3.45 (1H, s).

INTERMEDIATE 10

Methyl 2-(S)-benzyloxycarbonylamino-3-0.3-dimethyl-butanoate

MeOH (50 ml) was cooled to 0° C. under a nitrogen atmosphere before adding acetyl chloride (28.2 mmol, 2.22 g) and the mixture stirred for 5 min. A solution of N-benzyloxycarbonyl tert-leucine (11.3 mmol, 3 g) in MeOH (10 ml) was added, the reaction mixture warmed to RT, stirred for 18 hr, and the volatiles were removed in vacuo to give the title compound (2.8 g) as a white solid. $\delta_H$ (CDCl$_3$) 0.95 (9H, s), 3.7 (3H, s), 4.2 (1H, d), 5.10 (2H, s) and 7.35 (5H, m).

INTERMEDIATE 11

Methyl 2-(S)-amino-3.3-dimethylbutanoate

To a degassed solution of Intermediate 10 (7.16 mmol, 2 g) in MeOH (50 ml) were added Pd/C 10% (200 mg) and ammonium formate (35.8 mmol, 2.3 g). The reaction mixture was heated to reflux for 18 hr, then cooled and the catalyst filtered off through a cellite plug. The solvent was removed in vacuo to give the title compound (1.02 g) as a white solid. $\delta_H$ (CDCl$_3$) 1.0 (9H, s) and 3.8 (3H, s).

INTERMEDIATE 12

N$^4$-Hydroxy-N$^1$-(1-(S)-methoxycarbonyl-2.2-dimethylpropyl)-2-(R)-(4-chlorophenylpropyl)succinamide From Intermediate 7b) using the reagents and conditions described for the preparation of the compound of Example 1 according to method (i). $\delta_H$ (CDCl$_3$) 0.95 (9H, s), 1.5–1.7 (4H, m), 2.3 (1H, dd, J 4, 14Hz), 2.4–2.6 (3H, m), 2.7–2.9 (1H, m), 3.7 (3H, s), 4.4 (1H, d), 6.35 (1H, d), 7.05 (2H, d), and 7.25 (2H, d).

INTERMEDIATE 13

2-(S)-[5-(4-Chlorophenyl)-2-(R)-(hydroxyaminocarbonyl-methyl)pentanoyl]-3.3-dimethylbutanoic acid Lithium hydroxide (5.8 mmol, 0.24 g) was added to a solution of Intermediate 12 (1.45 mmol, 0.6 g) in MeOH (20 ml) and H$_2$O (2 ml) under a nitrogen atmosphere and at RT. The reaction mixture was left to stir at reflux for 18 hr, volatiles were removed in vacuo and the resultant product was partitioned between H$_2$O (40 ml) and EtOAc (60 ml). The layers were separated and the aqueous layer was extracted with EtOAc (2×40 ml). The combined organic layer was dried (MgSO$_4$), the solvent removed in vacuo to give the title compound (272 mg) as a pinkish/white solid. $\delta_H$ (CDCl$_3$) 1.0 (9H, s), 1.4–1.5 (1H, m), 1.55–1.7 (3H, m), 2.15 (1H, dd), 2.35 (1H, dd), 2.6 (2H, m), 2.9 (1H, m), 4.3 (1H, m), 7.15 (4H, m) and 8.05 (1H, d).

EXAMPLE 1

N$^4$Hydroxy-N$^1$-(1-(S)-carbamoyl-2.2-dimethylpropyl)-2-(R)-4(chlorophenylpropyl)succinamide Method (i)

To Intermediate 7a) (1.85 g, 4.83 mmol) in dry DMF (20 ml) under N$_2$ at −20° C. was added N-methylmorpholine (796 μl, 7.25 ml) and ethyl chloroformate (426 μl, 4.83 mmol). After 30 min, O-(Trimethylsilyl)-hydroxylamine (1.80 ml, 24.15 mmol) was added, the solution allowed to warm up to RT and stirred for 3 hr. The reaction mixture was poured into 1.0M HCl and EtOAc was added. The layers were separated and the acid layer was washed with EtOAc (5×50 ml). The combined organic layer was washed with NaHCO$_3$ (3×50 ml), brine (2×50 ml) and dried (MgSO$_4$). The solvent was removed in vacuo to give a white solid. This was precipitated from MeOH/ether to give the title compound as a white solid. $\delta_H$ (CD$_3$OD) 1.01 (9H, s), 1.39–1.70 (4H, m), 2.17 (1H, dd, J 6, 15 Hz), 2.57 (1H, dd, J 6, 15 Hz), 2.50–2.68 (2H, m), 2.83–2.95 (1H, m), 4.28 (1H, s), 7.13 (2H, d, J 6 Hz) and 7.22 (2H, d, J 6 Hz).

Method (ii)

From Intermediate 13 (95.4 mg) using aqueous ammonia, and similar reagents and conditions to those used for the preparation of Intermediate 8. The product was isolated to yield the title compound (67 mg) with the expected $^1$H NMR spectrum.

The following compounds of Examples 2 to 6 were obtained from the starting Intermediate shown by a similar multi-step process to that described for the preparation of the compound of Example 1, method (i) from Intermediate 2 and utilising the appropriate Intermediates, and amino acid or N-substituted amino acid starting materials shown:

EXAMPLE 2

N$^4$-Hydroxy-N$^1$-(1-(S)-carbamoyl-2.2-dimethylpropyl)-2-(R)-(phenylpropyl)succinamide, from Intermediate 3, and L-tert-leucinamide $\delta_H$ (CD$_3$OD) 1.01 (9H, s), 1.40–1.78 (4H, m), 2.20 (1H, dd, J 6, 15 Hz), 2.35 (1H, dd, J 6, 15 Hz), 2.84–2.93 (1H, m), 2.53–2.70 (2H, m), 4.28 (1H, s) and 7.05–7.25 (5H, m).

EXAMPLE 3

N$^4$Hydroxy-N$^1$-(1-(S)-carbamoyl-2.2-dimethylpropyl)-2-(R)-(4-methylphenylpropyl)succinamide from Intermediate 1, and L-tert-leucinamide $\delta_H$ (CD$_3$OD) 1.01 (9H, s), 1.40–1.70 (4H, m), 2.15–2.40 (2H, m) plus (3H, s) at 2.25, 2.45–2.65 (2H, m), 2.70–2.95 (1H, m), 4.28 (1H, s) and 7.02 (4H, s).

EXAMPLE 4

N$^4$-Hydroxy-N$^1$-(1-(S)-carbamoyl-2.2-dimethylpropyl)-2-(R)-(4-methoxyphenylpropyl)succinamide, from Intermediate 4, and L-tert-leucinamide δ$_H$ (CD$_3$OD) 1.01 (9H, s), 1.40–1.65 (4H, m), 2.18 (1H, dd, J 6, 15 Hz), 2.35 (1H, dd, J 6, 15 Hz), 2.45–2.60 (2H, m), 2.80–2.95 (1H, m), 3.73 (3H, s), 4.28 (1H, s), 6.78 (2H, d, J 8 Hz) and 7.06 (2H, d, J 8 Hz).

EXAMPLE 5

N$^4$-Hydroxy-N$^1$-(1-(S)-methylaminocarbonyl-2.2-dimethylpropyl)-2-(R)-(4-chlorophenylpropyl)succinamide, from Intermediate 2, and Intermediate 9

δ$_H$ (CD$_3$OD) 0.95 (9H, s), 1.40–1.65 (4H, m), 2.10–2.20 (1H, dd), 2.3–2.4 (1H, dd), 2.5–2.6 (2H, m), 2.7 (3H, s), 2.85 (1H, m), 4.25 (1H, s) and 7.15–7.3 (4H, dd).

EXAMPLE 6

N$^4$-Hydroxy-N$^1$-(1-(S)-carbamoyl-2.2-dimethylpropyl)-2-(R)-(4-fluorophenylpropyl)succinamide, from Intermediate 5, and L-tert-leucinamide δ$_H$ (CDCl$_3$) 1.01 (9H, s), 1.41–1.64 (4H, m), 2.17 (1H, dd, J 6.5, 14.6 Hz), 2.34 (1H, dd, J 8.0, 14.6 Hz), 2.57 (2H, m), 2.86 (1H, m) 4.27 (1H, s), 6.95 (2H, m) and 7.15 (2H, m).

EXAMPLE 7

N$^4$-Hydroxy-N$^1$-(1-(S)-methylaminocarbonyl-2.2-dimethylpropyl)-2-(R)-(4-methylphenylpropyl)succinamide From Intermediate 7c) using similar reagents and conditions to those described for the preparation of the compound of Example 1 method (i). δ$_H$ (CD$_3$OD) 0.95 (9H, s), 1.4–1.6 (4H, m), 2.15 (1H, dd, J 6, 15 Hz), 2.25 (3H, s), 2.3 (1H, dd, J 6, 15 Hz), 2.4–2.6 (2H, m), 2.65 (3H, s), 2.85 (1H, m), 4.2 (1H, s) and 7.0 (4H, m).

EXAMPLE A

The activity of the compounds of the invention may be determined as described below.

All enzyme assays to determine Ki values were performed using the peptide substrate Dnp-Pro-Leu-Gly-Leu-Trp-Ala-D-Arg-NH$_2$. [M. Sharon Stock and Robert D. Gray. JBC 264, 4277–81, 1989). The enzymes cleave at the Gly-Leu bond which can be followed fluorimetrically by measuring the increase in Trp fluorescence emission associated with the removal of the quenching dinitrophenol (Dnp) group.

Essentially, enzyme (e.g. gelatinase, stromelysin, collagenase) at 0.08–2 nM; a range of inhibitor concentrations (0.1–50×Ki) and substrate (approx. 20 μm) are incubated overnight in 0.1M Tris/HCl buffer, pH 7.5, containing 0.1M NaCl, 10 mM CaCl$_2$ and 0.05%. Brij 35 at either room temperature or 37° C. depending on the enzyme. The reaction is stopped by adjusting the pH to 4 using 0.1M sodium acetate buffer and the fluorescence read at an excitation wavelength of 280 nm and emission wavelength of 346 nm.

K$_i$ values can be established using the equation for tight-binding inhibition:

$$V_i = \frac{V_o}{2[E]} (\sqrt{(K_{i(app)} + [I])^2 + 2(K_{i(app)} - [I])[E] + [E]^2} - (K_{i(app)} + [I] - [E]))$$

where V$_o$ is the initial rate of reaction in the absence of inhibitor, V$_i$ is the initial rate in the presence of inhibitor, [E] is the total enzyme concentration and [I] the total inhibitor concentration in the reaction mixture.

For stromelysin and collagenase, K$_i$ (app) was assumed to approximate to the true K$_i$ as [S]<<K$_m$ for the substrate hydrolysis. For gelatinase the K$_i$ was determined by performing the analyses at several substrate concentrations. A plot of K$_i$(app) vs. [S] then gave the true K$_i$ as the value of the y-axis intercept.

The following results were obtained with compounds according to the invention:

| | Ki(nM) | | |
|---|---|---|---|
| Compound of Example No. | Collagenase | Stromelysin-1 | Gelatinase 72KD |
| 1 | 121.7 | 10.9 | 0.07 |
| 2 | NT | NT | 0.255 |
| 3 | 491 | 10.2 | 0.042 |
| 4 | NT | NT | 0.023 |
| 5 | 22.5 | 2.64 | 0.01 |
| 6 | NT | NT | 0.21 |
| 7 | 84.4 | 9.91 | 0.023 |

NT = not tested

EXAMPLE B

The oral activity of the compounds according to the invention may be determined using the pleural cavity assay described below.

A 2 ml solution of the test compound in an appropriate solvent (e.g. 50% polyethylene glycol (PG) plus a variable proportion of dimethyl sulphoxide (DMSO) (if required) is administered orally. After an interval of up to 24 hrs, 0.4 ml of a mixture of an equal volume (2.2 ml) of the enzyme gelatinase A (72 K form at a concentration of 20 nM) and radiolabelled [$^{14}$C]-gelatin (at an approximate concentration of 10 μM i.e. 500 times molar excess) is injected into the pleural cavity and maintained at 4° C. After 35 min mice are overdosed with anaesthetic, the contents of the pleural cavity aspirated and the aspirates cleared by centrifugation at 4° C. then diluted to 15% in trichloroacetic acid (TCA) and left overnight at 4° C. The resulting TCA precipitate is then separated by centrifugation and radioactivity in each supernatant measured by scintillation counting. Results are expressed as a % inhibition of enzyme activity calculated by comparing the radioactivity measured for each test compound with a control value obtained by performing the same assay in the absence of a gelatinase inhibitor.

The following results were obtained with compounds according to the invention:

| Compound of Example No. | % Inhibition (at 10 mg/Kg) |
|---|---|
| 1 | 100 |
| 2 | 73 |
| 3 | 95 |
| 4 | 82 |
| 5 | 64 |

-continued

| Compound of Example No. | % Inhibition (at 10 mg/Kg) |
|---|---|
| 6 | 76 |
| 7 | 100 (at 80 mg/Kg) |

A comparative experiment was carried out using the same procedure and the compound of Example 1 [A] and the amides [B], [C] and [D] (prepared in a similar fashion to the compound of Example 1):

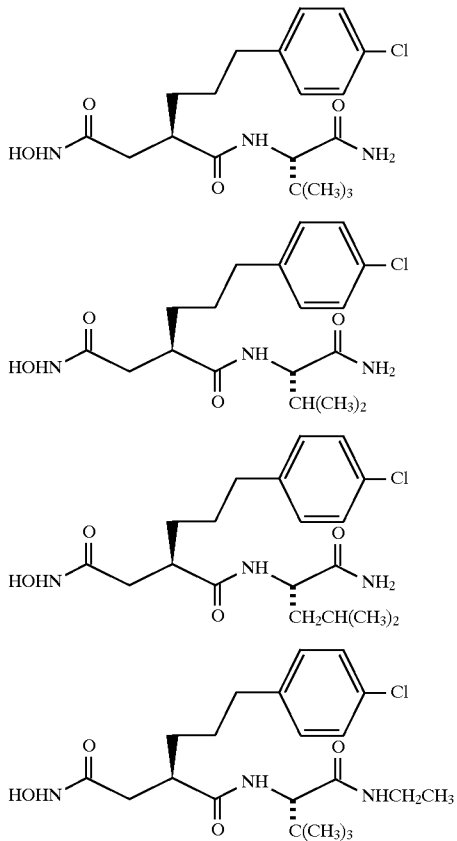

Each compound was administered at the same dose. Compound [A] gave 100% inhibition; Compound [B] gave 53% inhibition; Compound [C] gave 25% inhibition; and Compound [D] gave 11% inhibition. These results show the advantageously good oral bioactivity of the compound of the invention [A] when compared with the structurally closely related compounds [B], [C] and [D].

EXAMPLE C

The ability of compounds of the invention to inhibit angiogenesis was demonstrated in mice.

Compounds were assessed by their ability to inhibit vascularisation of sponge implants in mice. The amount of vascularisation in this model is determined by the rate of clearance of radioactive xenon from the sponge. Compounds in polyethylene glycol (PG) vehicle were orally administered twice per day at a dose of 100 mg/kg, with administration beginning 8 h after sponge implementation.

FIG. 1 illustrates the result of one experiment using the compound of Example 1. For comparative purposes the following compound (Compound [E]) was used:

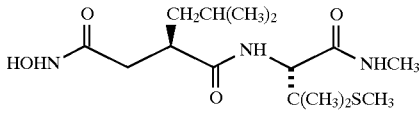

(prepared as described in International Patent Application No. PCT/GB 94/00896). Compound [E] is approximately 40 fold less potent on gelatinase than the compound of Example 1, and 40 fold more potent on collagenase than this compound of the invention.

The results are expressed in FIG. 1 as a graph of xenon clearance (expressed as a clearance constant) against time. The compound of Example 1 gave substantial inhibition of vascularisation as seen by the marked inhibition of xenon clearance, which was much greater than the inhibition achieved by the non-specific metalloproteinase inhibitor Compound [E].

We claim:

1. A compound of formula (1)

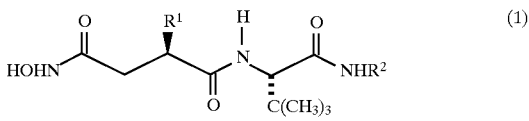

wherein $R^1$ represents

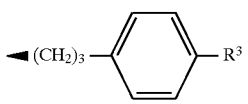

where $R^3$ is a hydrogen or halogen atom or a methyl, trifluoromethyl or a methoxy group;

$R^2$ represents a hydrogen atom or a methyl group; or a salt, solvate, hydrate or prodrug thereof.

2. A compound according to claim 1, wherein $R^2$ is a hydrogen atom.

3. A compound according to claim 1, wherein $R^3$ is a chlorine or fluorine atom or a methyl, trifluoromethyl or methoxy group.

4. A compound according to claim 3, wherein $R^3$ is a chlorine atom or a methyl or methoxy group.

5. A compound according to claim 1, selected from the group consisting of $N^4$-Hydroxy-$N^1$-(1-(S)-carbamoyl-2,2-dimethylpropyl)-2-(R)-(4-chlorophenylpropyl)succinamide;

$N^4$-Hydroxy-$N^1$-(1-(S)-carbamoyl-2,2-dimethylpropyl)-2-(R)-(4-methylphenylpropyl)succinamide;

$N^4$-Hydroxy-$N^1$-(1-(S)-carbamoyl-2,2-dimethylpropyl)-2-(R)-(4-methoxyphenylpropyl)succinamide;

$N^4$-Hydroxy-$N^1$-(1-(S)-carbamoyl-2,2-dimethylpropyl)-2-(R)-(4-trifluoromethylphenylpropyl)succinamide;

and the salts, solvates, hydrates and prodrugs thereof.

6. A compound according to claim 5, selected from the group consisting of:

$N^4$-Hydroxy-$N^1$-(1-(S)-carbamoyl-2,2-dimethylpropyl)-2-(R)-(4-chlorophenylpropyl)succinamide;

and the salts, solvates and hydrates thereof.

7. A pharmaceutical composition, comprising a compound according to claim 1, and a pharmaceutically acceptable diluent, carrier or excipient.

8. A process for preparing a compound of formula (1)

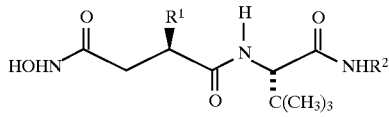 (1)

wherein R¹ represents

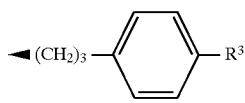

where $R^3$ is a hydrogen or halogen atom or a methyl, trifluoromethyl or methoxy group:

$R^2$ represents a hydrogen atom or a methyl group; and the salts, solvates, hydrates and prodrugs thereof, which comprises in a final step (a) reacting an acid of formula (2)

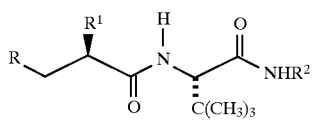 (2)

where R represents a —CO₂H group or an active derivative thereof, with hydroxylamine or an O-protected derivative or a salt thereof, followed where necessary by removal of any protecting group;

(b) reacting an acid of formula (7)

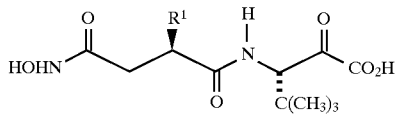 (7)

or an active derivative thereof with ammonia or methylamine; and/or (c) reacting a compound of formula (1) with an acid or base to yield the corresponding salt.

9. A method for the prophylaxis or treatment of an angiogenesis dependent disease in humans, which comprises administering an effective dose of a compound of formula (1):

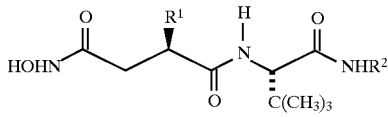 (1)

wherein R¹ represents

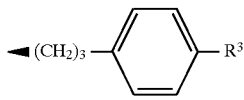

where $R^3$ is a hydrogen or halogen atom or a methyl, trifluoromethyl or methoxy group;

$R^2$ represents a hydrogen atom or a methyl group; or a salt, solvate, hydrate or prodrug thereof, to a subject with a disease associated with angiogenesis.

10. A method according to claim 9, wherein in said compound of formula (1), $R^2$ is a hydrogen atom.

11. A method according to claim 9, wherein in said compound of formula (1), $R^3$ is a chlorine or fluorine atom or a methyl, trifluoromethyl or methoxy group.

12. A method according to claim 11, wherein in said compound of formula (1), $R^3$ is a chlorine atom or a methyl or methoxy group.

13. A method according to claim 11, wherein said compound of formula (1) is selected from the group consisting of:

$N^4$-Hydroxy-$N^1$-(1-(S)-carbamoyl-2,2-dimethylpropyl)-2-(R)-(4-chlorophenylpropyl)succinamide;

$N^4$-Hydroxy-$N^1$-(1-(S)-carbamoyl-2,2-dimethylpropyl)-2-(R)-(4-methylphenylpropyl)succinamide;

$N^4$-Hydroxy-$N^1$-(1-(S)-carbamoyl-2,2-dimethylpropyl)-2-(R)-(4-methoxyphenylpropyl)succinamide;

$N^4$-Hydroxy-$N^1$-(1-(S)-carbamoyl-2,2-dimethylpropyl)-2-(R)-(4-trifluoromethylphenylpropyl)succinamide;

and the salts, solvates, hydrates and prodrugs thereof.

14. A method according to claim 11, wherein said compound of formula (1) is selected from the group consisting of:

$N^4$-Hydroxy-$N^1$-(1-(S)-carbamoyl-2,2-dimethylpropyl)-2-(R)-(4-chlorophenylpropyl)succinamide;

and the salts, solvates and hydrates thereof.

* * * * *